US012586275B2

(12) United States Patent
Miyazaki

(10) Patent No.: US 12,586,275 B2
(45) Date of Patent: Mar. 24, 2026

(54) X-RAY CT APPARATUS AND METHOD

(71) Applicant: CANON MEDICAL SYSTEMS CORPORATION, Tochigi (JP)

(72) Inventor: Hiroaki Miyazaki, Otawara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 247 days.

(21) Appl. No.: 18/475,592

(22) Filed: Sep. 27, 2023

(65) Prior Publication Data

US 2024/0104799 A1 Mar. 28, 2024

(30) Foreign Application Priority Data

Sep. 27, 2022 (JP) ................................. 2022-154102

(51) Int. Cl.
| | |
|---|---|
| *G06T 11/00* | (2006.01) |
| *A61B 6/00* | (2024.01) |
| *A61B 6/03* | (2006.01) |
| *A61B 6/42* | (2024.01) |
| *A61B 6/50* | (2024.01) |

(52) U.S. Cl.
CPC ............ *G06T 11/005* (2013.01); *A61B 6/032* (2013.01); *A61B 6/4241* (2013.01); *A61B 6/481* (2013.01); *A61B 6/488* (2013.01); *A61B 6/504* (2013.01)

(58) Field of Classification Search
CPC ....... A61B 6/032; A61B 6/4241; A61B 6/481; A61B 6/488; A61B 6/504; A61B 6/482
See application file for complete search history.

(56) References Cited

U.S. PATENT DOCUMENTS

| | | | |
|---|---|---|---|
| 11,717,242 B2 | 8/2023 | Gatayama et al. | |
| 2016/0089100 A1* | 3/2016 | Korporaal | A61B 6/541 |
| | | | 600/431 |
| 2017/0238896 A1* | 8/2017 | Iwai | A61B 6/4035 |
| 2020/0337668 A1 | 10/2020 | Grass et al. | |
| 2022/0096028 A1* | 3/2022 | Gatayama | G01T 1/17 |

FOREIGN PATENT DOCUMENTS

| | | | |
|---|---|---|---|
| JP | 3678382 B2 * | 8/2005 | |
| JP | 2009-261519 A | 11/2009 | |
| JP | 2021-510583 A | 4/2021 | |
| JP | 2022-57301 A | 4/2022 | |

* cited by examiner

*Primary Examiner* — Casey Bryant

(74) *Attorney, Agent, or Firm* — Oblon, McClelland, Maier & Neustadt, L.L.P.

(57) ABSTRACT

An X-ray CT apparatus according to an embodiment includes a photon counting detector that outputs a signal that enables measurement of an energy value of an X-ray photon incident thereon, and processing circuitry configured to determine a time to make a transition from a prescan to a main scan by estimating, from projection data, an amount of a contrast agent present on an X-ray path including a monitored region set for a subject in the prescan, the projection data having been generated by detection of X-rays by the photon counting detector, the X-rays having been transmitted through the monitored region.

12 Claims, 4 Drawing Sheets

ROI: THRESHOLD
EXCEEDED
START IMAGING

FIG.1

ROI: THRESHOLD
EXCEEDED
START IMAGING

X-RAY CT APPARATUS AND METHOD

CROSS-REFERENCE TO RELATED APPLICATIONS

This application is based upon and claims the benefit of priority from Japanese Patent Application No. 2022-154102, filed on Sep. 27, 2022; the entire contents of which are incorporated herein by reference.

FIELD

Embodiments described herein relate generally to X-ray CT apparatuses and methods.

BACKGROUND

Contrast agents may be used in examinations using X-ray computed tomography (CT) apparatuses. Contrast agents are preferably used less because using large amounts of contrast agents may cause side effects in subjects. However, reducing the amount of a contrast agent used shortens the time period over which a target to be examined, such as a blood vessel, is contrast-enhanced and makes adjustment of when to execute a CT scan difficult.

A method of executing a prescan before a main CT scan has been known as a technique for executing CT scans at appropriate times. Specifically, in a known method, X-ray CT images (image data) are sequentially generated in a prescan, changes in pixel values of a region of interest that is a target to be examined or of a region near the region of interest are monitored, and a main scan is started when inflow of a contrast agent is detected on the basis of the changes in the pixel values.

BRIEF DESCRIPTION OF THE DRAWINGS

FIG. 1 is a block diagram illustrating an example of a configuration of an X-ray CT apparatus according to an embodiment;

DETAILED DESCRIPTION

Figure 2:
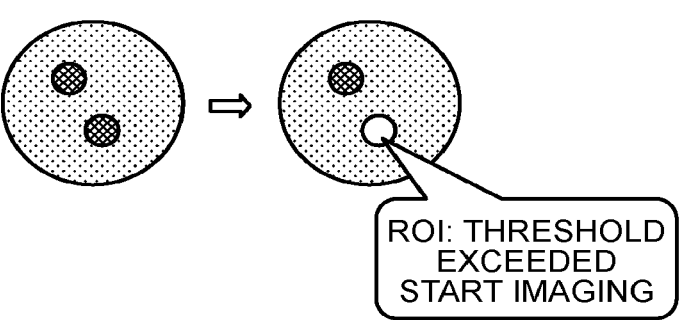
FIG. 2 is a diagram for description of a region of interest and a monitored region, according to the embodiment.

An X-ray CT apparatus according to the embodiment comprises a photon counting detector and processing circuitry. The photon counting detector is configured to output a signal that enables measurement of an energy value of an X-ray photon incident on the photon counting detector. The processing circuitry is configured to determine a time to make a transition from a prescan to a main scan by estimating, from projection data, an amount of a contrast agent present on an X-ray path including a monitored region set for a subject in the prescan, the projection data having been generated by detection of X-rays by the photon counting detector, the X-rays having been transmitted through the monitored region.

Embodiments of the X-ray CT apparatus and a method will hereinafter be described in detail by reference to the appended drawings.

Figure 1:
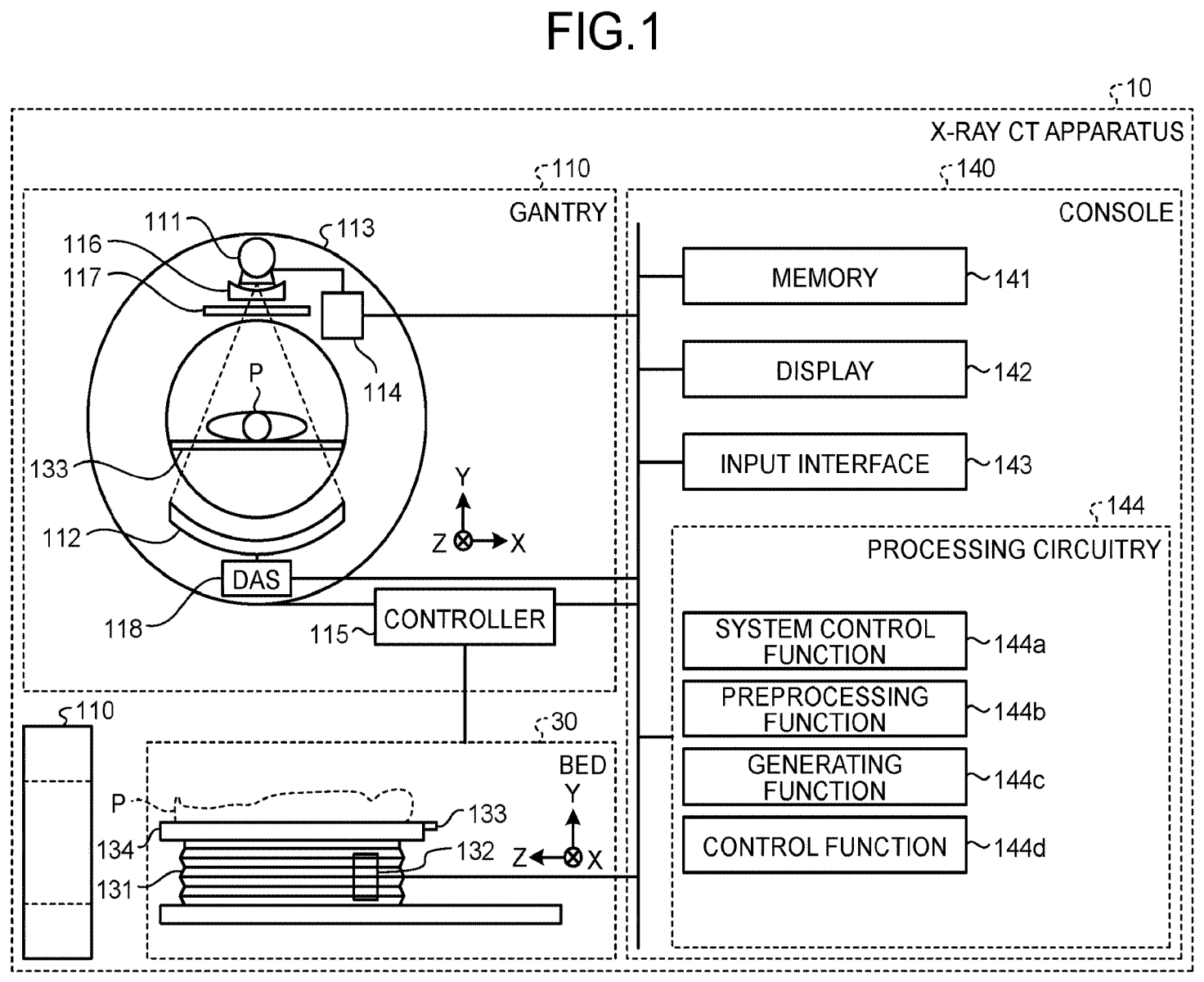

An X-ray CT apparatus 10 will be described by use of FIG. 1. FIG. 1 is a block diagram illustrating an example of a configuration of the X-ray CT apparatus 10 according to an embodiment. As illustrated in FIG. 1, the X-ray CT apparatus 10 has a gantry 110, a bed 130, and a console 140.

In FIG. 1, a rotation axis of a rotation frame 113 in a non-tilted state or a longitudinal direction of a tabletop 133 of the bed 130 is along a Z-axis. An axis orthogonal to the Z-axis and horizontal to a floor surface is an X-axis. An axis orthogonal to the Z-axis and vertical to the floor surface is a Y-axis. FIG. 1 depicts, for the sake of description, the gantry 110 from plural directions and illustrates a case where the X-ray CT apparatus 10 has one gantry 110.

The gantry 110 has an X-ray tube 111, an X-ray detector 112, the rotation frame 113, an X-ray high voltage generator 114, a controller 115, a wedge 116, a collimator 117, and a data acquisition system (DAS) 118.

The X-ray tube 111 is a vacuum tube having: a cathode (filament) that generates thermions; and an anode (target) that receives collision of the thermions and generates X-rays. The X-ray tube 111 generates X-rays, with which a subject P is irradiated, by emitting thermions from the cathode to the anode through application of high voltage from the X-ray high voltage generator 114.

The X-ray detector 112 is a detector of the photon counting type and every time an X-ray photon enters the X-ray detector 112, the X-ray detector 112 outputs a signal enabling an energy value of the X-ray photon to be measured. The X-ray photon is, for example, an X-ray photon that has been emitted from the X-ray tube 111 and transmitted through the subject P. The X-ray detector 112 has plural detection elements. Each of the detection elements outputs an electric signal (analog signal) of one pulse every time an X-ray photon enters the detection element. Counting the number of electric signals (pulses) enables counting of the number of X-ray photons that have entered each of the detection elements. Performing a calculation process with these signals enables measurement of energy values of the X-ray photons that have caused the signals to be output. For example, the X-ray detector 112 is an area detector having plural detection elements that have been arranged in a channel direction and a slice direction.

The above described detection elements each include, for example, a scintillator and an optical sensor, such as a photomultiplier. In this case, the X-ray detector 112 serves as an indirect conversion type detector that converts an X-ray photon incident on the X-ray detector 112 to scintillation light by means of the scintillator and converts the scintillation light into an electric signal by means of the optical sensor, such as the photomultiplier. The above described detection elements each have, for example, an electrode arranged on a semiconductor detection element of, for example, cadmium telluride (CdTe) or cadmium zinc telluride (CdZnTe). In this case, the X-ray detector 112 serves as a direct conversion type detector that directly converts X-ray photons incident on the X-ray detector 112 into electric signals.

The X-ray detector 112 has: the above described detection elements; and plural application specific integrated circuits (ASICs) that are connected to the detection elements and count X-ray photons detected by the detection elements. The ASICs count the numbers of X-ray photons that have entered the detection elements by performing discrimination of individual electric charges output by the detection elements. Furthermore, by performing a calculation process based on the individual electric charges, the ASICs measure energy of the X-ray photons that have been counted. The ASICs also output, as digital data, results of the counting of the X-ray photons, to the DAS 118.

The rotation frame 113 is an annular frame that supports the X-ray tube 111 and the X-ray detector 112 opposite to each other and rotates the X-ray tube 111 and the X-ray detector 112 by means of the controller 115. For example, the rotation frame 113 is a casting made of a material including aluminum. The rotation frame 113 may also support, in addition to the X-ray tube 111 and the X-ray detector 112: the X-ray high voltage generator 114; the wedge 116; the collimator 117; and/or the DAS 118, for example. Furthermore, the rotation frame 113 may also support any of various components not illustrated in FIG. 1. The rotation frame 113 and parts that rotationally move with the rotation frame 113, in the gantry 110, will hereinafter be also referred to as a rotation unit.

The X-ray high voltage generator 114 has: a high voltage generator that has electric circuitry including a transformer and a rectifier and generates high voltage to be applied to the X-ray tube 111; and an X-ray controller that controls output voltage according to X-rays to be generated by the X-ray tube 111. The high voltage generator may be of the transformer-type or the inverter-type. The X-ray high voltage generator 114 may be provided on the rotation frame 113 or on a fixed frame not illustrated in the drawings.

The controller 115 has: processing circuitry having a central processing unit (CPU); and a drive mechanism, such as a motor and an actuator. The controller 115 controls operation of the gantry 110 and the bed 130 by receiving input signals from an input interface 143. For example, the controller 115 controls rotation of the rotation frame 113, tilting of the gantry 110, and operation of the bed 130 and the tabletop 133. The controller 115 may be provided on the gantry 110 or the console 140.

The wedge 116 is a filter for adjusting the quantity of X-rays emitted from the X-ray tube 111. Specifically, the wedge 116 is a filter that transmits and attenuates X-rays therethrough, the X-rays having been emitted from the X-ray tube 111, so that X-rays emitted from the X-ray tube 111 to the subject P have a predetermined distribution. For example, the wedge 116 is a wedge filter or a bow-tie filter, and is a filter made of aluminum that has been processed to achieve a predetermined target angle and/or have a predetermined thickness.

The collimator 117 is, for example, lead plates for narrowing down the range irradiated with X-rays that have been transmitted through the wedge 116 and includes a combination of plural lead plates, the combination forming a slit. The collimator 117 may be called an X-ray diaphragm. In FIG. 1, the wedge 116 is arranged between the X-ray tube 111 and the collimator 117, but the collimator 117 may be arranged between the X-ray tube 111 and the wedge 116. In this case, the wedge 116 transmits and attenuates X-rays therethrough, the X-rays having been emitted from the X-ray tube 111 and limited in their irradiation range by the collimator 117.

The DAS 118 collects signals of X-rays detected by the detection elements included in the X-ray detector 112. For example, the DAS 118 has an amplifier that performs amplification processing of an electric signal output from each detection element and an A/D converter that converts the electric signal to a digital signal. The DAS 118 thereby generates detection data. The DAS 118 is implemented by, for example, a processor.

Data generated by the DAS 118 are transmitted, by optical communication, from a transmitter having a light emitting diode (LED) provided on the rotation frame 113, to a receiver provided in a non-rotating part (for example, a fixed frame, which is not illustrated in FIG. 1) of the gantry 110 and having a photodiode, and the transmitted data are transferred from the receiver to the console 140. This non-rotating part is, for example, the fixed frame that rotatably supports the rotation frame 113. The data from the rotation frame 113 to the non-rotating part of the gantry 110 are not necessarily transmitted by optical communication, and any non-contact type data transmission method may be adopted or a contact-type data transmission method may be adopted.

The bed 130 is an apparatus on which the subject P who is a target to be scanned is placed and which moves the subject P, and has a base 131, a bed driver 132, the tabletop 133, and a support frame 134. The base 131 is a housing that supports the support frame 134 such that the support frame 134 is movable in a vertical direction. The bed driver 132 is a drive mechanism that moves the tabletop 133 having the subject P placed thereon, along a longitudinal axis of the tabletop 133, and includes a motor and an actuator, for example. The tabletop 133 provided on an upper surface of the support frame 134 is a plate where the subject P is placed. The bed driver 132 may move, in addition to the tabletop 133, the support frame 134 along the longitudinal axis of the tabletop 133.

The console 140 has a memory 141, a display 142, the input interface 143, and processing circuitry 144. The console 140 is described herein to be separately bodied from the gantry 110, but the console 140 or part of the components of the console 140 may be included in the gantry 110.

The memory 141 is implemented by, for example: a semiconductor memory element, such as a RAM or a flash memory; a hard disk; or an optical disk. The memory 141 stores therein, for example, projection data, and image data that have been reconstructed on the basis of the projection data. Furthermore, for example, the memory 141 stores therein a program for the circuitry to implement its functions, the circuitry being included in the X-ray CT apparatus 10. The memory 141 may also be implemented by the cloud.

The display 142 displays thereon various types of information. For example, the display 142 displays thereon various images generated by the processing circuitry 144 and displays thereon a GUI for receiving various operations from an operator. For example, the display 142 is a liquid crystal display or a CRT display. The display 142 may be of the desktop type, or may be, for example, a tablet terminal that is able to wirelessly communicate with the console 140.

The input interface 143 receives various input operations from an operator, converts the input operations received, into electric signals, and outputs the electric signals to the processing circuitry 144. For example, the input interface 143 is implemented by any of, for example: a mouse and a keyboard; a trackball; switches; buttons; a joystick; a touchpad enabling an input operation by a touch on an operation surface; a touchscreen having a display screen and a touchpad that have been integrated with each other; non-contact input circuitry using an optical sensor; and voice input circuitry. The input interface 143 may be provided on the gantry 110. Furthermore, the input interface 143 may be, for example, a tablet terminal that is able to wirelessly communicate with the console 140. The input interface 143 does not necessarily include physical operation parts, such as a mouse and a keyboard. Examples of the input interface 143 also include electric signal processing circuitry that receives an electric signal corresponding to an operation input from an external input device provided separately from the console 140 and outputs the electric signal to the processing circuitry 144.

The processing circuitry 144 controls the overall operation of the X-ray CT apparatus 10 by executing a system control function 144a, a preprocessing function 144b, a generating function 144c, and a control function 144d.

For example, the processing circuitry 144 executes a scan of the subject P by reading a program corresponding to the system control function 144a from the memory 141 and executing the program. For example, the system control function 144a supplies high voltage to the X-ray tube 111 by controlling the X-ray high voltage generator 114. The X-ray tube 111 thereby generates X-rays to be emitted to the subject P. Furthermore, the system control function 144a moves the subject P into a gantry aperture of the gantry 110 by controlling the bed driver 132. Furthermore, the system control function 144a adjusts the size and position of the slit in the collimator 117. The system control function 144a rotates the rotation unit by controlling the controller 115. The DAS 118 collects signals of X-rays from the detection elements in the X-ray detector 112 and generates detection data while a scan is executed by the system control function 144a.

Furthermore, the processing circuitry 144 performs preprocessing of detection data output from the DAS 118 by reading and executing a program corresponding to the preprocessing function 144b from the memory 141. For example, the preprocessing function 144b performs preprocessing, such as logarithmic transformation processing, offset correction processing, inter-channel sensitivity correction processing, and beam hardening correction, of the detection data output from the DAS 118. Data that have been subjected to the preprocessing will also be referred to as raw data. Furthermore, the detection data that have not been subjected to the preprocessing yet and the raw data that have been subjected to the preprocessing will also be collectively referred to as projection data.

The processing circuitry 144 generates image data (volume data) on the basis of projection data by reading and executing a program corresponding to the generating function 144c from the memory 141. For example, the generating function 144c reconstructs the image data by performing reconstruction processing of the projection data, the reconstruction processing using, for example, filtered back projection or iterative reconstruction.

Furthermore, for example, the processing circuitry 144 determines when to make a transition from a prescan to a main scan by reading and executing a program corresponding to the control function 144d from the memory 141. The control function 144d is an example of a control unit. The system control function 144a firstly starts a prescan of the subject P and makes a transition from the prescan to a main scan at a time determined by the control function 144d. Details of processing performed by the control function 144d will be described later.

In the embodiment, a main scan is a scan to collect projection data to be used in X-ray interpretation. Image data are reconstructed from projection data collected by a main scan, and the image data reconstructed are referred to by a medical doctor for, for example, a diagnosis and a treatment plan.

A prescan is a scan executed before a main scan for determination of a time at which a transition is to be made to the main scan. Projection data collected by a prescan may be used or not used in X-ray interpretation. The prescan is usually executed at a dose lower than that for the main scan.

In the X-ray CT apparatus 10 illustrated in FIG. 1, the processing functions have been stored in the memory 141, in the form of programs that are executable by a computer. The processing circuitry 144 is a processor that implements the functions corresponding to the programs by reading and executing the programs from the memory 141. In other words, the processing circuitry 144 that has read the programs has the functions corresponding to the read programs.

In FIG. 1, the processing circuitry 144 singly implements the system control function 144a, the preprocessing function 144b, the generating function 144c, and the control function 144d, but the processing circuitry 144 may include a combination of plural independent processors and these processors may execute the programs to implement the functions. Furthermore, any of the processing functions of the processing circuitry 144 may be implemented by being distributed to plural pieces of processing circuitry or being integrated into a single piece of processing circuitry, as appropriate.

The term, "processor", used above means, for example: a CPU; a graphics processing unit (GPU); or a circuit, such as an application specific integrated circuit (ASIC) or a programmable logic device (for example, a simple programmable logic device (SPLD), a complex programmable logic device (CPLD), or a field programmable gate array (FPGA)). The processor implements the functions by reading and executing the programs stored in the memory 141.

In FIG. 1, the memory 141 singly stores the programs corresponding to the processing functions. However, the embodiment is not limited to this example. For example, in a configuration that may be adopted instead, plural memories 141 are dispersedly arranged and the processing circuitry 144 reads corresponding programs from the individual memories 141. Furthermore, instead of being stored in the memory 141, the programs may be directly incorporated in circuitry of the processor. In this case, by reading and executing the programs incorporated in the circuitry, the processor implements the functions.

The processing circuitry 144 may implement a function by using a processor of an external device connected via a network NW. For example, the processing circuitry 144 may implement the functions illustrated in FIG. 1 by reading and executing the programs corresponding to the functions from the memory 141 and using a computational resource that is a server group (the cloud) connected to the X-ray CT apparatus 10 via the network NW.

The overall configuration of the X-ray CT apparatus 10 has been described above. The X-ray CT apparatus 10 configured as described above enables a time to be readily determined in an examination using a contrast agent, the time being a time at which a transition is to be made to a main scan.

The following description is on an example of a method of determining a time at which a transition is to be made to a main scan. In an examination using the X-ray CT apparatus 10, a region of interest is firstly set. A region of interest is a region that a user, such as a medical doctor, is interested in, in the subject P, and is for example, an affected region or a region suspected to be affected. A contrast agent is used in a case where the region of interest is a heart or a blood vessel, because a simple CT scan will not visualize such region of interest in the image data.

In a case where a CT scan is performed using a contrast agent, the scan is preferably started by determination of a time at which the region of interest is permeated with the contrast agent. Using a large amount of the contrast agent increases the time period over which the region of interest is permeated with the contrast agent and thus facilitates acquisition of image data in the state where the region of interest is permeated with the contrast agent, but side effects of using the large amount of the contrast agent on the subject P are a concern. Continuously performing the CT scan for a long period of time facilitates the acquisition of the image data in the state where the region of interest is permeated with the contrast agent, but the increase in radiation exposure of the subject P is also a concern. Therefore, to reduce the amount of the contrast agent used and the radiation exposure of the subject P, a scan is preferably: started by determination of an appropriate time at which the region of interest is permeated with the contrast agent; and completed in a short period of time.

Executing a prescan before a main CT scan may be considered for executing the CT scan at an appropriate time. For example, the system control function 144a firstly starts a prescan of the subject P. Specifically, the system control function 144a causes the X-ray tube 111 to emit X-rays to the subject P while causing the X-ray tube 111 to rotate around the subject P. X-rays that have been transmitted through the subject P are detected by the X-ray detector 112 and projection data of various irradiation angles (views) are thereby generated. The generating function 144c reconstructs image data on the basis of the projection data.

In a prescan, collection of projection data and reconstruction of image data are sequentially performed. That is, the generating function 144c generates a time series of plural sets of image data on the basis of a time series of plural sets of projection data collected in a prescan. The control function 144d determines a time to make a transition from a prescan to a main scan, on the basis of such a time series of plural sets of image data. For example, as illustrated in FIG. 2, the control function 144d starts imaging when a pixel value in a monitored region exceeds a threshold.

A monitored region may be, as illustrated in FIG. 2, a region of interest (ROI) or a region near the region of interest. For example, when a right atrium is a region of interest, the control function 144d may set the right atrium as a monitored region or set the vena cava that allows blood to flow into the right atrium as the monitored region. The pixel value to be used for comparison with the threshold may be a CT value or a gradation value converted from the CT value, the gradation value being for a display image.

The threshold may be a preset value or a value adjusted by a user as appropriate. For example, a threshold may be empirically set for each combination of a region of interest and a monitored region. Specifically, a threshold is able to be optimized by raising the threshold in a case where a transition from a prescan to a main scan is performed using the threshold and the transition is found to be too early, and lowering the threshold in a case where the transition is found to be too late.

In a case where a monitored region is a region near a region of interest, the control function 144d is able to determine a time at which a transition is to be made to a main scan by calculating a time period from inflow of the contrast agent into the monitored region to inflow of the contrast agent into the region of interest, on the basis of the distance between the monitored region and the region of interest and the flow velocity of the blood, for example. In a case where the monitored region is the region of interest, the control function 144d is able to determine a time at which a transition is to be made to a main scan by calculating a time period from the first inflow of the contrast agent into the region of interest to diffusion of the contrast agent throughout the region of interest, on the basis of the size of the region of interest and the flow velocity of the blood, for example.

In a case where a time point at which the control function 144d determines a time to make a transition to a main scan is before that time determined, the system control function 144a waits until the determined time before starting the main scan. However, due to the calculation time period for reconstruction processing, for example, the time point at which the control function 144d determines the time for the transition to the main scan may be after that determined time. In this case, promptly after the control function 144d determines the time for the transition to the main scan, the system control function 144a starts the main scan.

As described above, monitoring a change in a pixel value in a monitored region of image data collected in a prescan and detecting inflow of the contrast agent enable determination of a time for a transition to a main scan. However, generating the image data requires a certain period of time. For example, reconstruction processing is unable to be performed unless projection data corresponding to "360°" have been collected in a case where full reconstruction is performed, and projection data corresponding to "180°+fan angle" have been collected in a case where half reconstruction is performed. Furthermore, the calculation time period for the reconstruction processing is also needed. Therefore, in some cases, a main scan is unable to be started at an appropriate time due to a time lag generated between inflow of a contrast agent into a monitored region and determination of a time for a transition to the main scan.

Furthermore, artefacts may be generated in image data (for example, metal artefacts). Prescans are usually performed at a dose lower than that for a main scan and artefacts thus tend to be generated more in prescans. Various reconstruction methods for reducing artefacts have been proposed, but reducing artefacts by a reconstruction method is difficult because reconstruction processing needs to be completed quickly to reduce the above described time lag. When image data include artefacts, the artefacts may be erroneously determined as inflow of a contrast agent and a main scan may be unable to be started at an appropriate time.

Therefore, the X-ray CT apparatus 10 readily determines a time to make a transition to a main scan, on the basis of projection data, without performing reconstruction processing.

Figure 3:
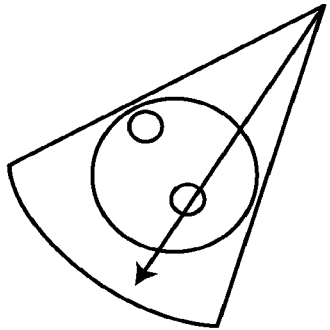
FIG. 3 is a diagram for description of projection data according to the embodiment.

Specifically, in a prescan, for example, as illustrated in FIG. 3, irradiation of the subject P with X-rays is performed such that the X-rays are transmitted through a monitored region in the subject P. Projection data are generated by the X-ray detector 112 detecting the X-rays that have been transmitted through the monitored region.

For example, the system control function 144a causes the X-ray tube 111 to emit X-rays to the subject P while causing the X-ray tube 111 to rotate around the subject P. Because reconstructable projection data (for example, projection data corresponding to "360°" and projection data corresponding to "180°+fan angle") do not need to be collected, the system control function 144a may reduce the radiation exposure by performing the irradiation with X-rays intermittently.

For example, the system control function 144a causes the X-ray tube 111 to emit X-rays when the X-ray tube 111 is positioned at a predetermined irradiation angle. That is, the system control function 144a causes the X-ray tube 111 to emit X-rays every time the X-ray tube 111 has rotated once around the subject P. In this case, the projection data collected are all data of the same irradiation angle. The control function 144d estimates an amount of the contrast agent present every time a set of projection data is collected and compares the amount with a threshold. Details of this process will be described later. There may be influence of movement made by the subject P, but collecting plural sets of projection data at the same irradiation angle enables uniformization of calculation conditions for estimation of the amount of the contrast agent present.

The system control function 144a may collect projection data without including any bones in the X-ray path. For example, in a case where projection data are collected for the abdomen, irradiating the subject P with X-rays from left and right (that is, irradiating the patient P with X-rays at 90°) enables collection of projection data without including any bones, such as bones in the spine, in the path of the X-rays. There is thereby no need to set "bone (calcium)" in a substance discrimination process described later and calculation is thus facilitated.

One may consider collecting projection data in a prescan by causing the X-ray tube 111, which has been fixed, to emit X-rays without rotating the rotation unit including the X-ray tube 111. However, in this case, upon a transition to a main scan, a time period for accelerating the rotation unit to a predetermined rotation velocity is needed. If the acceleration of the rotation unit is unable to be completed within a time period between determination of a time for the transition to the main scan and the time determined, the rotation unit is preferably rotated in the prescan.

In another example, the system control function 144a may cause irradiation with X-rays every given time period or every given angle. In this case, the projection data collected are data of various irradiation angles. Increasing the X-ray irradiation intervals enables more reduction of the radiation exposure of the subject P. On the contrary, decreasing the X-ray irradiation intervals enables accurate determination of a time for a transition from the prescan to a main scan, by later described estimation of the amount of the contrast agent present and comparison with a threshold on a shorter cycle.

FIG. 3 illustrates an example where a range including a monitored region is irradiated with fan beam X-rays, but the later described estimation of the amount of the contrast agent present is able to be executed if projection data corresponding to one path (data corresponding to one detection element) through the monitored region are available. That is, the system control function 144a may collect projection data using laser X-rays having a fan angle of approximately 0. For example, the system control function 144a may set a fan angle such that the monitored region is included in the X-ray irradiation range even if there is influence of movement made by the subject P and may cause a narrow range to be irradiated with X-rays, the narrow range including the monitored region.

A monitored region is able to be set, for example, on the basis of image information collected beforehand. Examples of this image information may include X-ray CT images collected beforehand, a low dose 3D landmark scan that is a helical scan for positioning, and three-dimensional scanograms.

Furthermore, a monitored region may also be set without using image information. That is, a monitored region may be set from anatomic knowledge on positional relations between various organs and blood vessels.

In a case where a substance having a high absorption coefficient (for example, a medical device, such as a pacemaker, or a metallic fixator) is inside the body of the subject P, the substance and a monitored region preferably do not overlap each other. This is because signals detected are weakened by large attenuation of X-rays and accuracy of calculation in the later described estimation of the amount of the contrast agent present may be reduced. In a case where image information that has been collected beforehand is available, the position of the monitored region and the X-ray irradiation angle are able to be adjusted on the basis of the image information so that the substance having a high absorption coefficient and the monitored region do not overlap each other.

In a case where a substance having a high absorption coefficient is known to be inside the body of the subject P and image information collected beforehand is not available, image data may be reconstructed on the basis of projection data collected in a prescan and the position of the substance having the high absorption coefficient may be determined. This prescan is a non-contrast-enhanced (non-CE) scan and blood vessels are not visualized in the image data reconstructed.

In a case where projection data of various irradiation angles have been collected and the various irradiation angles include an irradiation angle at which a substance having a high absorption coefficient and a monitored region overlap each other, the projection data of that irradiation angle may be not used in the later described estimation of the amount of the contrast agent present. For example, in a case where the projection data collected include a portion having a CT value exceeding the threshold (for example, a CT value corresponding to a metal), the projection data may be not used in the later described estimation of the amount of the contrast agent present.

Subsequently, the control function 144d obtains a count for each energy bin from the projection data and estimates an amount of the contrast agent present by a substance discrimination process. For example, by solving Equation (1) and Equation (2) below, the control function 144d estimates the amount of each of two substances present.

$$N(\mathrm{bin1})=N0(\mathrm{bin1})\times\exp(-(u1(\mathrm{bin1})L1+u2(\mathrm{bin1})L2)) \qquad (1)$$

$$N(\mathrm{bin2})=N0(\mathrm{bin2})\times\exp(-(u1(\mathrm{bin2})L1+u2(\mathrm{bin2})L2)) \qquad (2)$$

Two energy bins have been set in Equation (1) and Equation (2). In Equation (1) and Equation (2), "N(bin1)" is a count for an energy bin, "bin1". That is, "N(bin1)" is the number of X-ray photons having X-ray energy included in the energy bin, "bin1", in X-ray photons incident on the X-ray detector 112. Similarly, "N(bin2)" is a count for an energy bin, "bin2". In Equation (1) and Equation (2): "u1(bin1)" represents a linear attenuation coefficient for the energy bin, "bin1", for a substance 1; "u2(bin1)" represents a linear attenuation coefficient for the energy bin, "bin1", for a substance 2; "u1(bin2)" represents a linear attenuation coefficient for the energy bin, "bin2", for the substance 1; and "u2(bin2)" represents a linear attenuation coefficient for the energy bin, "bin2", for the substance 2. Values of these linear attenuation coefficients are known.

In Equation (1) and Equation (2), "L1" is a path length over which the substance 1 is present, and "L2" is a path length over which the substance 2 is present. By solving Equation (1) and Equation (2), "L1" and "L2" are able to be found. For example, in a case where an iodine based contrast agent is used, Equation (1) and Equation (2) are able to be solved, with the substance 1 being "water" and the substance 2 being "iodine".

Every time a set of projection data is collected, the control function 144d solves Equation (1) and Equation (2) to find a path length of the contrast agent (the path length, "L2", of "iodine"). For example, the path length of the contrast agent is approximately 0 before the contrast agent flows into the monitored region. Thereafter, inflow of the contrast agent into the monitored region increases the path length of the contrast agent. Depending on whether or not the path length of the contrast agent has exceeded the threshold, the control function 144d is able to determine a time to make a transition from the prescan to a main scan.

A path length of a contrast agent is not limited to actual presence of the contrast agent over a range corresponding to that path length. For example, in a case considered now for the sake of description, a contrast agent has flown into a blood vessel having a thickness, "2 mm", and the concentration of the contrast agent has become "10%" by mixing with blood. In this case, the path length of the contrast agent is calculated to be "0.2 mm" that is "10%" of "2 mm", but the contrast agent is actually dispersedly present over a range of "2 mm".

In the above described example, a path length of a contrast agent is compared with a threshold, but the embodiment is not limited to this example. For example, if the thickness, "2 mm", of a blood vessel is already known, as described above, the path length, "0.2 mm", of the contrast agent corresponds to "10%". This ratio of the path length to the thickness of the blood vessel may be compared with a threshold to determine a time to make a transition from the prescan to a main scan.

A path length of a contrast agent and a ratio of the path length to a thickness of a blood vessel are examples of the amount of the contrast agent present. That is, examples of the amount of the contrast agent present are not limited to the mass or volume of the contrast agent and include various parameters that change according to increase and decrease of the contrast agent. For example, the amount of the contrast agent evidently increases as the path length of the contrast agent increases. Any parameter that has a correlation with increase and decrease in the amount of the contrast agent is included in examples of the amount of the contrast agent present.

Figure 4:
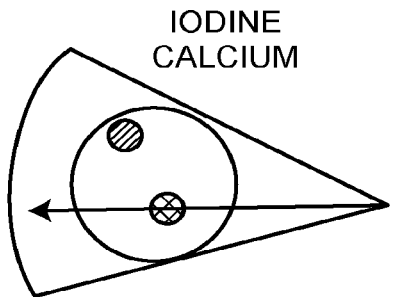
FIG. 4 is a diagram illustrating an example of a substance discrimination process according to the embodiment.

In the above described example, two substances are set and the amount of each of these substances present is estimated, but the number of substances to be set may be optionally modified. For example, for the chest or the head, as illustrated in FIG. 4, a "bone" is often included in the X-ray irradiation range. Therefore, "bone (calcium)" is added as a substance 3 to the above described "water" and "iodine" in calculation, and the amount of each of these substances present may be calculated. In principle, the number of substances that can be set is not limited, and setting the number of energy bins corresponding to the number of substances enables the simultaneous equations to be solved.

In the above described example, the path length of each substance is found by simultaneous equations like Equation (1) and Equation (2), but the embodiment is not limited to this example. For example, an energy bin corresponding to a contrast agent may be set and the amount of the contrast agent present may be estimated on the basis of a count for the energy bin. For example, finding a correlation between counts in an energy bin and amounts of a contrast agent present beforehand enables: conversion of a count for the energy bin to an amount of the contrast agent present; and use of the amount for comparison with a threshold.

Figure 5A:
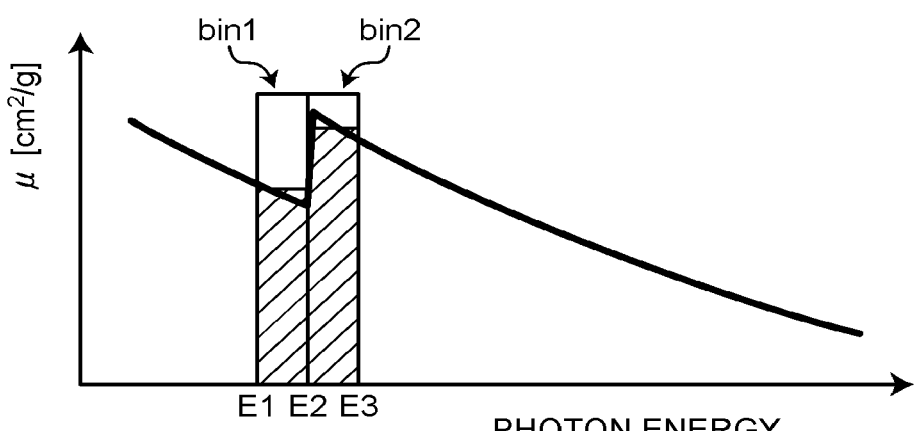
FIG. 5A is a diagram illustrating an example of setting of energy bins, according to the embodiment.
Figure 5B:
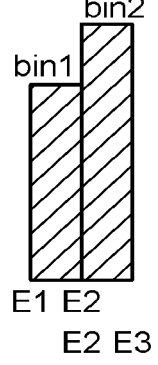
FIG. 5B is a diagram illustrating the example of the setting of the energy bins, according to the embodiment.

Plural energy bins corresponding to one contrast agent may be set and a value calculated from counts for the energy bins may be used for comparison with a threshold. For example, for some contrast agents, a k-edge like that illustrated in FIG. 5A and FIG. 5B is observed. Setting two energy bins before and after the k-edge and finding a difference between counts for these energy bins enables obtainment of an enhanced value of the k-edge.

Specifically, in FIG. 5A and FIG. 5B, when a k-edge is at energy E2, an energy bin, "bin1", from energy E1 to the energy E2 is set as a first energy bin and an energy bin, "bin2", from the energy E2 to energy E3 is set as a second energy bin. If a contrast agent has been present on the X-ray path, the difference between the count for the energy bin, "bin1", and the count for the energy bin, "bin2", is large. On the contrary, if the contrast agent has not been present, no k-edge is observed and the difference between the count for the energy bin, "bin1", and the count for the energy bin, "bin2", is small. As described above, the difference between the count for the energy bin, "bin1", and the count for the energy bin, "bin2", is an example of the amount of the contrast agent present, and comparing the amount with a threshold enables determination of a time to make a transition from the prescan to a main scan.

In a case where sets of projection data of various irradiation angles are collected, substances included in the X-ray paths and the amounts of noise vary among the sets of projection data. The accuracy may thereby vary in the above described estimation of the amount of the contrast agent present. Therefore, the control function 144d may bundle plural sets of projection data of different irradiation angles to mitigate influence of the variation in the substances included in the X-ray paths and the amounts of noise. For example, the control function 144d may perform averaging of the counts for the energy bins of a few views that are adjacent to each other and perform the above described estimation of the amount of the contrast agent present, with the noise reduced.

As described above, the X-ray CT apparatus 10 of the embodiment includes the X-ray detector 112 of the photon counting type that outputs signals enabling measurement of energy values of X-ray photons incident on the X-ray detector 112, and the control function 144d that determines a time to make a transition from the prescan to a main scan. The control function 144d estimates the amount of the contrast agent present on the X-ray path including a monitored region, from projection data generated by detection of X-rays by the X-ray detector 112, the X-rays having been transmitted through the monitored region set for the subject P in the prescan, and thereby determines a time to make a transition from the prescan to a main scan. Therefore, the X-ray CT apparatus 10 of the embodiment is able to readily determine the time to make a transition to a main scan, without any reconstruction processing.

Furthermore, the omission of reconstruction processing enables the X-ray CT apparatus 10 to quickly determine whether or not the contrast agent has flown into the monitored region. As described above, if time is needed for reconstruction processing, a time lag is generated between the inflow of the contrast agent into the monitored region and the determination of the time for the transition to the main scan and the main scan may thus be unable to be started at the appropriate time. That is, by the time the time to make the transition to the main scan is determined, the time determined may have passed already. Processing by the X-ray CT apparatus 10 of the embodiment is thus speeded up by the omission of reconstruction processing, the time lag is thereby shortened, and the transition to the main scan at the appropriate time is thus enabled.

Artefacts may be generated or enhanced in reconstruction processing, and this is particular prominent in a case where reconstruction processing is performed quickly. With the X-ray CT apparatus 10 of the embodiment, the omission of reconstruction processing enables reduction of influence of artefacts and accurate determination of the time for the transition to the main scan.

The X-ray CT apparatus 10 of the embodiment intermittently performs irradiation with X-rays to collect projection data and is able to determine a time to make a transition from the prescan to a main scan on the basis of the projection data. That is, because the projection data are not used for reconstruction processing, the number of sets of projection data to be collected is able to be decreased and radiation exposure of the subject P is able to be reduced.

In the case described above with respect to the embodiment, one type of contrast agent is injected, but the embodiment is not limited to this case. That is, in a case where plural types of contrast agents are injected, a time to execute a main scan may be determined for each of the contrast agents.

For example, a first contrast agent that is iodine based and a second contrast agent that is gadolinium based may be injected into the subject P. Comparing the amount of the first contrast agent present with a threshold enables: determination of a time to make a transition to a first main scan; and acquisition of image data having blood vessels contrast-enhanced for a monitored region. Comparing the amount of the second contrast agent present with a threshold enables: determination of a time to make a transition to a second main scan; and acquisition of image data having the second contrast agent accumulated in a specific part (for example, a lesion) in the monitored region.

As described above, without performing reconstruction processing, the control function 144d is able to determine, on the basis of projection data, a time to make a transition from a prescan to a main scan. The control function 144d may also perform reconstruction processing and determine, on the basis of image data, a time to make a transition from a prescan to a main scan. The control function 144d may perform switch-over between these methods as appropriate.

The method of determining a time to make a transition to a main scan on the basis of projection data has many advantages, including: being simple and enabling processing to be speeded up; enabling accurate determination of the time due to the speeded up processing, and enabling intermittent X-ray irradiation to be sufficient and thus radiation exposure to be reduced. However, with no reconstruction processing and thus no acquisition of three-dimensional information, in a case where shapes of the blood vessels are complex, for example, the monitored region may be unable to be identified. For example, in a case where a blood vessel is set as a monitored region, whether a contrast agent has flown into the blood vessel or the contrast agent has just flown into a blood vessel near that blood vessel may be unable to be determined. In this case, the control function 144d may perform reconstruction processing, distinguish between these blood vessels on the basis of three-dimensional image data, and determine a time to make a transition from the prescan to a main scan. This switch-over between the methods may be automatically done by the control function 144d on the basis of complexity of the shapes of the blood vessels, or a user, such as a medical doctor, may manually perform the switch-over between these methods.

In the above described embodiment, the types of the contrast agents are not particularly limited, and a positive contrast agent having, for example, iodine or barium sulfate as a main component may be used or a gaseous contrast agent, such as carbon dioxide, may be used. The injection of the contrast agent may be manually performed by a user, such as a medical doctor, or automatically performed by an injector provided in the X-ray CT apparatus 10.

In the case described above with respect to the embodiment, the amount of the contrast agent present on the X-ray path including the monitored region is estimated, the estimated amount present is compared with the threshold, and the time to make a transition from the prescan to a main scan is determined. However, the embodiment is not limited to this case. For example, on the basis of the rate of increase (temporal gradient) in the estimated amount present, a time to make a transition from the prescan to a main scan may be determined.

In the example described above with respect to the embodiment, discrimination of substances in the projection data is performed using the X-ray detector 112 of the photon counting type. However, as long as discrimination of substances in projection data is possible, the embodiment is not limited to the use of the X-ray detector 112 of the photon counting type. For example, the X-ray CT apparatus 10 may implement the above described embodiment by performing dual energy imaging, collecting high energy/low energy projection data, and performing a substance discrimination process.

For example, the X-ray CT apparatus 10 may include a layered detector as the X-ray detector 112. The layered detector includes a first layer and a second layer, disperses X-rays emitted from the X-ray tube 111, and detects the X-rays dispersed. For example, the first layer detects low energy X-rays and the second layer detects high energy X-rays that have been transmitted through the first layer. High energy projection data are then able to be obtained on the basis of output from the first layer and low energy projection data are able to be obtained on the basis of output from the second layer.

The components of each apparatus or device according to the embodiment described above have been functionally and conceptually illustrated in the drawings and are not necessarily configured physically as illustrated in the drawings. That is, specific forms of distribution and integration of each apparatus or device are not limited to those illustrated in the drawings, and all or part of each apparatus or device may be configured to be distributed or integrated functionally or physically in any units, according to various loads and/or use situations, for example. Furthermore, all or any part of the processing functions executed in each apparatus or device may be implemented by a CPU and a program or programs analyzed and executed by the CPU or may be implemented as hardware by wired logic.

Furthermore, the methods described above with respect to the embodiment may be implemented by a computer, such as a personal computer or a workstation, executing a program that has been prepared beforehand. This program may be provided via a network, such as the Internet. Furthermore, this program may be recorded in a computer-readable non-transitory recording medium, such as a hard disk, a flexible disk (FD), a CD-ROM, an MO, or a DVD, and executed by being read by a computer from the recording medium.

At least one embodiment described above enables a time to be determined readily, the time being a time at which a transition is to be made to a main scan, in an examination using a contrast agent.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:

a photon counting detector configured to output a signal that enables measurement of an energy value of an X-ray photon incident on the photon counting detector; and processing circuitry configured to determine a time to make a transition from a prescan to a main scan by estimating, from projection data, an amount of a contrast agent present on an X-ray path including a monitored region set for a subject in the prescan, the projection data having been generated by detection of X-rays by the photon counting detector, the X-rays having been transmitted through the monitored region.

2. The X-ray CT apparatus according to claim 1, wherein the processing circuitry is further configured to determine the time to make the transition from the prescan to the main scan by comparing the estimated amount to a threshold.

3. The X-ray CT apparatus according to claim 1, wherein the processing circuitry is further configured to estimate the amount by obtaining a count for each energy bin from the projection data and performing a substance discrimination process.

4. The X-ray CT apparatus according to claim 1, wherein the processing circuitry is further configured to estimate the amount based on a count for an energy bin corresponding to the contrast agent.

5. The X-ray CT apparatus according to claim 4, wherein the processing circuitry is further configured to set, as the energy bin corresponding to the contrast agent, two energy bins before and after a k-edge for the contrast agent.

6. The X-ray CT apparatus according to claim 1, wherein the projection data include plural sets of projection data collected for an irradiation angle that is identical for all of the plural sets of projection data.

7. The X-ray CT apparatus according to claim 1, wherein the projection data are collected at an irradiation angle at which no bones of the subject are included in the X-ray path.

8. The X-ray CT apparatus according to claim 1, wherein the monitored region is set such that a substance having a high absorption coefficient inside a body of the subject is not included in the X-ray path, or the projection data are collected at an irradiation angle at which the substance is not included in the X-ray path.

9. The X-ray CT apparatus according to claim 1, wherein the projection data are collected while an X-ray tube is rotated around the subject.

10. The X-ray CT apparatus according to claim 1, wherein the main scan is a scan to collect projection data used in X-ray interpretation.

11. A method, including:

determining a time to make a transition from a prescan to a main scan by estimating, from projection data, an amount of a contrast agent present on an X-ray path including a monitored region set for a subject in the prescan, the projection data having been generated by detection of X-rays by a photon counting detector, the X-rays having been transmitted through the monitored region.

12. The method of claim 11, wherein the determining step further comprises determining the time to make the transition without performing reconstruction processing.

* * * * *